United States Patent [19]

White et al.

[11] Patent Number: 5,762,869

[45] Date of Patent: Jun. 9, 1998

[54] BLOOD OXYGENATOR

[75] Inventors: George W. White, Lake Forest; Brian M. Raze, Corona; Jeffrey P. Du Montelle, Irvine, all of Calif.

[73] Assignee: Gish Biomedical, Inc., Irvine, Calif.

[21] Appl. No.: 685,358

[22] Filed: Jul. 24, 1996

[51] Int. Cl.$^6$ .................................................. A61M 1/14
[52] U.S. Cl. .............................. 422/48; 422/46; 422/45
[58] Field of Search ............................ 422/43, 46, 48; 604/4

[56] References Cited

U.S. PATENT DOCUMENTS

| | | | |
|---|---|---|---|
| 3,422,008 | 1/1969 | McLain | 210/646 |
| 3,794,468 | 2/1974 | Leonard | 422/48 |
| 3,807,958 | 4/1974 | Brumfield et al. | 422/46 |
| 4,065,264 | 12/1977 | Lewin | 422/46 |
| 4,254,081 | 3/1981 | Streczyn et al. | 422/46 |
| 4,344,777 | 8/1982 | Siposs | 96/206 |
| 4,368,118 | 1/1983 | Siposs | 210/136 |
| 4,424,190 | 1/1984 | Mather, III et al. | 422/46 |
| 4,602,965 | 7/1986 | Fukusawa et al. | 422/46 |
| 4,639,353 | 1/1987 | Takemura et al. | 422/46 |
| 4,690,758 | 9/1987 | Leonard et al. | 210/247 |
| 4,698,207 | 10/1987 | Bringham et al. | 422/46 |
| 4,902,416 | 2/1990 | Schroeder et al. | 210/321.67 |
| 5,026,479 | 6/1991 | Bikson et al. | 210/321.8 |
| 5,240,677 | 8/1993 | Jones et al. | 422/46 |
| 5,346,621 | 9/1994 | Haworth et al. | 210/645 |
| 5,376,334 | 12/1994 | Haworth | 422/46 |
| 5,421,405 | 6/1995 | Goodin et al. | 165/154 |
| 5,462,619 | 10/1995 | Haworth | 156/172 |

FOREIGN PATENT DOCUMENTS 04129565  4/1992  Japan.

OTHER PUBLICATIONS

JAPIO abstract of JP04129565 (Yasushi et al.), Apr. 30, 1992.

*Primary Examiner*—Robert J. Warden
*Assistant Examiner*—Alex Noguerola
*Attorney, Agent, or Firm*—George F. Bethel; Patience K. Bethel

[57] ABSTRACT

A blood oxygenator having a housing with an outer walled portion and a top portion and bottom portion. Blood is introduced through the bottom portion of the housing to be oxygenated by a fiber bundle having blood and oxygen flow. A blood outlet manifold in the upper portion of the housing is connected to a blood outlet on one end having a conical passage. The blood outlet manifold includes a reservoir with an increasing volume toward the conical passage and is sloped upwardly to enhance gaseous microemboli disentrainment. The wall of the housing decreases in dimension upwardly toward the blood outlet manifold, while the introduction of blood to the fibers is in a lesser ratio to the area adjacent the outlet manifold.

27 Claims, 4 Drawing Sheets

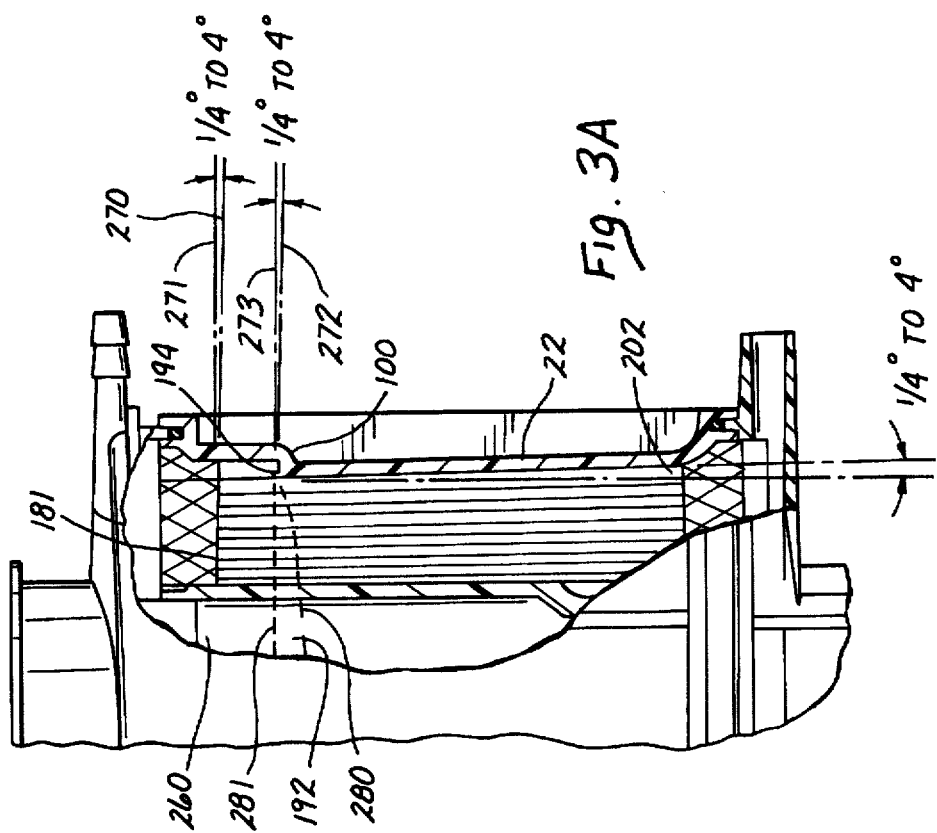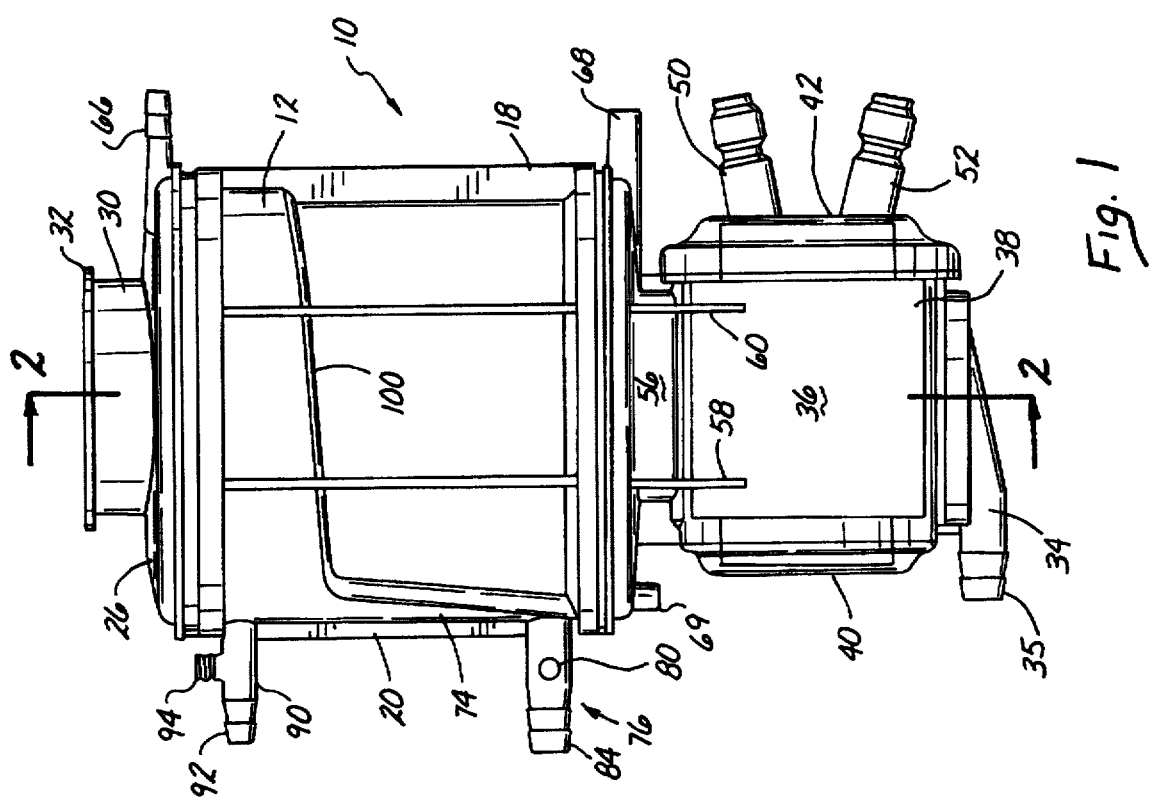

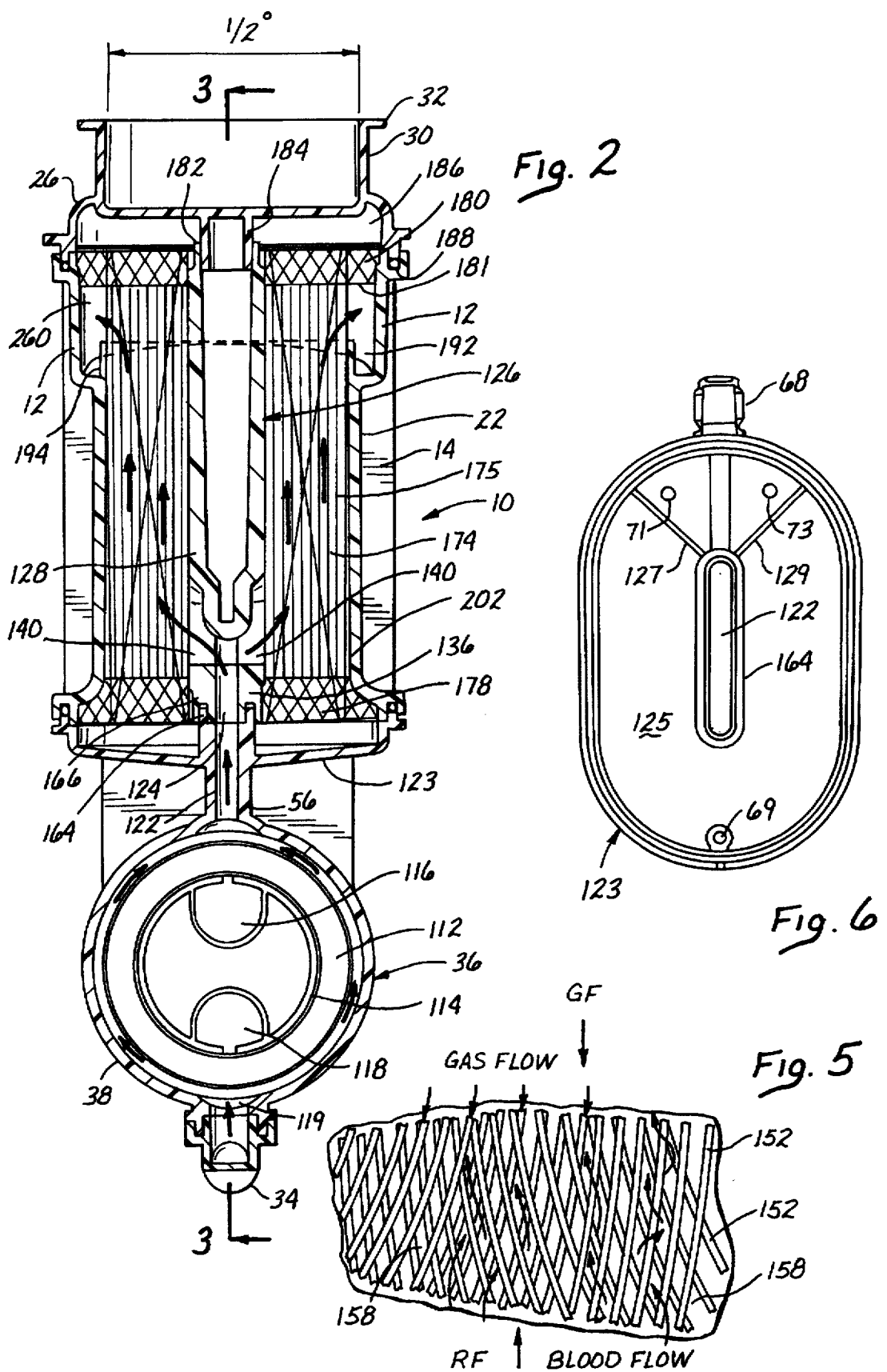

BLOOD OXYGENATOR

FIELD OF THE INVENTION

The field of this invention is within the extracorporeal bypass circuit art employing a series of interconnected medical devices. These medical devices temporarily function as a patient's heart and lungs. They serve to circulate, add oxygen to, and remove carbon dioxide from the patient's blood while the patient's own heart and lungs are inactive while on cardiopulmonary or extracorporeal bypass (on bypass), typically during open heart surgery.

Within that circuit, generally, a blood oxygenator is utilized.

More specifically, the field relates to a blood oxygenator which enables gas exchange of oxygen and carbon dioxide and serves to regulate the temperature of the patient's blood.

PRIOR ART

The prior art of blood oxygenators (oxygenators) within an extracorporeal bypass circuit employs interconnected specialty medical devices which circulate, add oxygen to, and remove carbon dioxide from the patient's blood while the patient's own heart and lungs are inactive.

During bypass surgery, a patient's blood is routed through such medical devices which replicate the functions of the heart and lungs. The principal blood handling components of this circuit include various tubing systems, an oxygenator, an arterial filter, and a venous reservoir. The primary components of such devices including the oxygenator are generally single use disposable products.

One of the key elements in the system is an oxygenator. The oxygenator enables gas exchange of oxygen and carbon dioxide with the patient's blood. It also cooperatively regulates the temperature of a patient's blood by having a heat exchanger in association with it. Although, the heat exchanger need not be integral to or with the oxygenator, it has been found that an integrated oxygenator including a heat exchanger is preferred in many cases.

In conjunction with the oxygenator, a venous reservoir is utilized in order to provide for a consistent flow of blood.

Also connected to, and in conjunction with the oxygenator, is an arterial filter. The arterial filter is specifically designed to trap and remove air, and filter out microemboli from the blood.

All of the foregoing key components of an extracorporeal circuit for open heart surgery and similar operations greatly rely upon the oxygenator for oxygenating the blood. As a consequence, the oxygenator is not only a key component, but a highly specialized, designed, and integrated unit for the circuitry which must function within various parameters.

Some of these parameters when the oxygenator is functioning with an integrated heater include keeping the blood at a particular desired temperature. Also, the blood must be oxygenated to a certain degree and at a certain rate to provide for blood flow that would fundamentally be analogous to a person's normal oxygenated arterial blood. To do this, a plurality of tubules or fibers in a fiber bundle have been used in the prior art to exchange oxygen traveling through the tubules or fibers with blood in association therewith. Certain designs of the prior art incorporated various flow techniques. These flow techniques have been radial in nature, sometimes axial in nature, and sometimes a combination thereof.

Numerous flow techniques have been utilized in order to enhance transfer of the oxygen to the blood. However, it has been found that such techniques have not always been sufficient to optimize the transfer of the oxygen to the blood.

To further complicate this process, it is desirable that during priming and while on bypass that there be a minimum amount of bubbles or other free gas within the blood. This of course is to prevent injury to the patient.

An arterial filter is generally utilized in order to eliminate such gaseous microemboli in the blood. However, it has been found that relying upon the arterial filter alone without pre-treating the blood to eliminate bubbles, is not as effective. In effect, blood delivered to the arterial filter should be of a nature whereby the filter does not have to significantly function to eliminate gases from the blood. Thus, the combination of an efficient and gaseous microemboli eliminating oxygenator is a desirable key component to the circuit.

The prior art does not function to provide a readily efficient oxygenator. In effect, the prior art delivers oxygenated blood without the efficiencies of the oxygenator of this invention. It is believed that the particular design of this oxygenator with the gaseous microemboli removal means is a broad step over the art. This is enhanced by the nature of the orientation, and the overall design of the delivery of blood from a blood heater/cooler to the major portion of the oxygenator. It is further enhanced by conducting the blood in a substantially active flow while at the same time providing for the elimination of gas bubbles from the blood during priming and bypass.

The oxygenator activity in the form of this invention enhances the operational features of the foregoing by creating an elliptical and conical shape to the internal gas transfer bundle housing to improve performance and reduce the shunting of blood. A blood manifold space at the top of the bundle of tubules or fibers creates a relative reduction in blood velocity in relationship to the manifold space to help remove gaseous microemboli. This is a function of the reduced blood pressure created in the blood manifold. Additionally, the orientation of the fibers exiting the bundle, allows for a higher rate of utilization of the fiber bundle in regard to the oxygen to blood gas transfer.

A further feature which is advanced over the prior art is a blood manifold space that allows for gas removal due to the natural buoyancy of the gas bubbles.

Another drawback of the prior art was the difficulty in priming the unit. With this invention, the location of the blood ports and the respective vents allow for the oxygenator to be filled from the bottom to the top which allows for enhanced priming.

Another feature, previously referred to that overcomes deficiencies of the prior art, is an elongated elliptically shaped heat exchanger blood outlet. This optimizes heat exchange while at the same time allowing flow to an elliptically shaped bundle of tubules or fibers that transfer the oxygen to the blood across a broad segment thereof.

All of the foregoing elements substantially allow this invention to operate more efficiently and effectively over the prior art. Consequently, it is believed that this invention in light of the following specification has numerous patentable features.

SUMMARY OF THE INVENTION

In summation, this invention comprises a significantly improved oxygenator incorporating improved gas to blood transfer ratios with lower entrainment of gaseous microemboli during priming and on bypass and includes improved heat transfer and gas transfer elements in combination with each other to provide for oxygenated blood for delivery to a patient undergoing bypass surgery.

More particularly, the invention incorporates an oxygenator within a cardiovascular circuit that functions to deliver the desired oxygenated low gaseous microemboli arterial filter and in conjunction with a venous reservoir to re-circulate the blood. The venous reservoir can be incorporated and be connected to the oxygenator of this invention.

The invention incorporates an elliptically and conically shaped internal gas bundle housing of gas transfer tubules or fibers in a manner which reduces the shunting of blood through the bundle. The elongated elliptically shaped heat exchanger blood outlet connected to the fiber bundle creates optimum heat exchange efficiency and flow through the elliptically shaped fiber bundle. This is caused by initial radial flow at the lower portion and then axial flow through the bundle.

An improved blood manifold space at the top of the bundle of fibers reduces the pressure drop of the unit to allow a reduction in relative blood velocity to improve gaseous microemboli removal.

The outlet of the open fiber bundle tubules with its greater surface area reduces pressure drop and optimizes maximum utilization of the fiber bundle as will be seen hereinafter in the specification.

The blood manifold space at the upper portion of the pack of tubules has an angular configuration which aids in priming and gaseous microemboli removal. The configuration is such where it allows the downward flow of blood toward the outlet while at the same time allowing the natural buoyancy of the gases to help in gaseous microemboli removal.

The angular configuration of the inlets and outlets with respect to the potting end seals provides for an internal orientation such where optimum flow of blood and disentrainment of gaseous microemboli is accomplished. This is due to the orientation of the upper portion of the gas exchange bundle and the lower portion sealing the tubules or bundle together within particular angular ranges to allow for optimum introduction and removal of gaseous microemboli from the oxygenated blood.

The foregoing features as summarized hereinbefore will become more apparent in the specification as it deals particularly with the details of the invention hereinafter.

BRIEF DESCRIPTION OF THE DRAWINGS

FIG. 1 shows a side elevation view of the oxygenator of this invention.

FIG. 2 shows a sectional view illustrating the blood flow through the oxygenator along lines 2—2 of FIG. 1.

FIG. 3A is a partially sectioned view from a portion of FIG. 3 showing the details thereof with respect to their angular orientation.

FIG. 5 shows the bundle of fibers taken from a fragmented portion of the bundle of tubules or fibers which constitute the oxygen to blood transfer media.

FIG. 6 shows a sectional view along lines 6—6 of FIG. 3 looking downwardly at the base of the oxygenator.

DETAILED DESCRIPTION OF THE PREFERRED EMBODIMENTS

Figure 3:
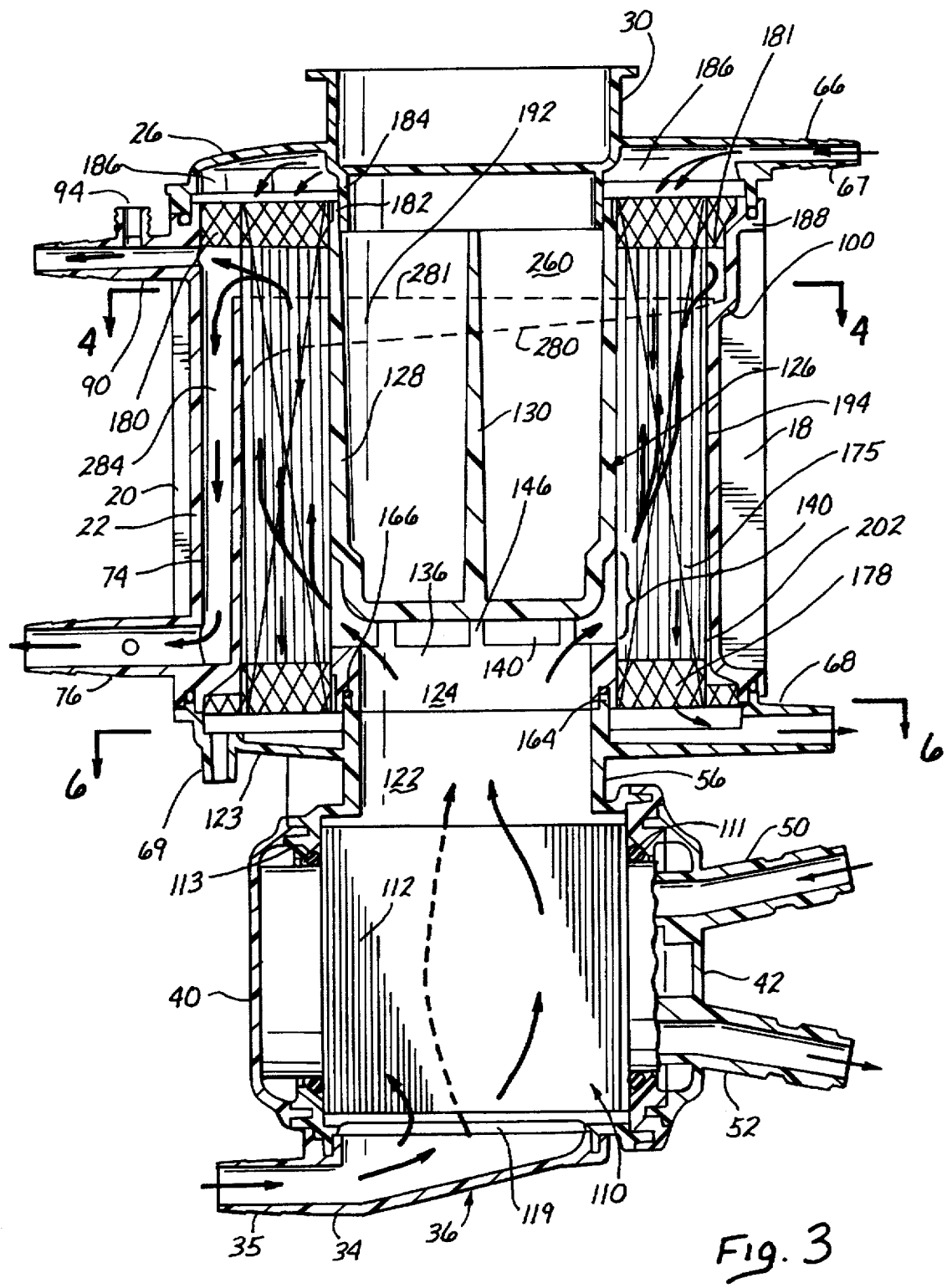
FIG. 3 is a mid-line sectional view of the oxygenator taken along lines 3—3 of FIG. 2.

Starting with FIG. 1 which shows an overall side elevation view of the oxygenator and the heat exchanger, it can be seen that a main housing 10 is shown. The main housing 10 serves as a hollow fiber housing. It also incorporates a core and the double walled features as will be seen hereinafter. An expanded outer double wall 12 is shown which houses an elongated elliptical trough, groove or reservoir for blood which can be seen in greater detail in FIGS. 3A, 4, 4A and 4B. This trough or reservoir as detailed hereafter serves in part to create the improved elements of this invention.

The housing 10 has ribs 14, 16, 18 and 20 as well as ribs analogous to ribs 14 and 16 on the opposite side. These ribs reinforce the housing so that a housing wall 22 circumscribing the housing 10 is reinforced. The ribs also serve to form a rigid structure for the entire housing 10.

An upper portion cap or top of the housing 10, seated on the outer wall 12, is shown. This upper portion or cap includes a top closure cap or lid 26. The lid 26 as will be seen is sealed and connected to the outer wall 12 to provide a gas upper or introductory manifold of this invention for the introduction of gas such as oxygen, which will be seen in the cross-sectional view.

On top of the lid 26 is a rounded cylindrical seat 30 with a flange 32. The rounded cylindrical seat 30 with the flange 32 may receive a venous reservoir thereon. The flange 32 can incorporate a bayonet type fitting with interior segmented flange elements or tabs which receive the venous reservoir. The orientation of the venous reservoir on top of the cylindrical seat 30 provides for ease of connection to the venous blood inlet as will be described hereinafter by serving to allow a flow of blood through a tubular member connected thereto.

In reference to the venous inlet, this can be seen as venous blood inlet conduit or port 34 having a barbed connection 35 which is known in the art for connecting a tube thereto. The tube is connected to the venous reservoir or any other venous blood supply which is to be oxygenated.

The venous inlet 34 extends upwardly to flow into the base of a heat exchanger 36 having a housing 38 in the form of a rounded cylindrical casing. At either end of the heat exchanger housing 38 are end caps 40 and 42. End caps 40 and 42 serve to enclose a series of heat exchange ribs or radial circular members, which will be seen in greater detail in FIGS. 2 and 3.

The heat exchanger housing end cap 42 incorporates an inlet connection, opening or inlet water vent 50 and an outlet connection, water vent or outlet 52. These respective inlet and outlet connections 50 and 52 provide for the delivery of temperature controlled water for warming or cooling the blood passing through the heat exchanger 36. The interior structure of the heat exchanger will be detailed hereafter.

The housing 10 is seated on the heat exchanger 36 and supported by means of a blood inlet portion which will be detailed hereinafter. The blood inlet portion is of the elliptical form previously mentioned, and is seen as the blood inlet within an outer elliptical wall 56. The connection, or the blood inlet wall 56 is reinforced by ribs 58 and 60 on either side which allow for support and reinforcement of the entire unit of the heat exchanger 36 and housing 10 for strength and resiliency.

The housing 10 is provided with a gas port or oxygen inlet 66 with a barbed connection 67 for the receipt of a tube connected to an oxygen supply. The release of the gas is through a gas outlet, or port 68. The respective gas inlet and gas outlet 66 and 68 cause the oxygen to flow through the fiber bundle tubules and oxygenate the blood as will be detailed hereinafter.

The blood flows through the oxygenator housing 10 to be oxygenated in the manner described hereinafter. It then flows downwardly through a conical outlet chamber seen within a doubled walled conical chamber, or funnel portion 74. This blood flow extends and flows outwardly through an arterial outlet or port 76. The outlet 76 has an arterial sample port 80 in order to sample blood to determine the extent of oxygenation during the oxygenation process. The arterial outlet 76 is provided with a barbed fitting 84 in order to connect an arterial tubing set or tube to the arterial filter or other portions of the system during an operation.

An auxiliary port, or outlet vent, 90 is shown having barbed fittings 92. The auxiliary port 90 is for venting gas or in some cases blood to another location. In order to vent the gas, a purge line is attached to a vent connection 94. The purge line is connected to a one way duck bill check valve to allow for the purging of gas which has been released and is no longer entrained in the blood flowing through the housing 10. This will be seen in connection with a blood manifold which is a substantial feature of this invention as detailed hereinafter.

The outlet 90 can also be used for priming the unit or for any other series of multiple outlet purposes.

Finally, as to the housing 10, it can be seen that the outside double wall 12 is shown sloping toward an outer wall base, step, ledge or indentation 100 to the funnel portion 74. This can be seen in greater detail in FIGS. 3, 4A and 4B, showing the interior portion of the double wall extending toward the direction of the funnel 74 for the removal of blood from the housing 10.

Looking more specifically at FIGS. 2 and 3 it can be seen wherein major sectional views of the oxygenator have been shown. These sectional views through the oxygenator show the flow of blood by the larger or thicker arrows with the flow of gas being shown by the smaller or less thick arrows. Concomitantly with this, it can be seen wherein the blood and oxygen is flowing through the fiber bundle in a detailed general axial flow manner.

Looking at FIG. 3 in particular, it can be seen that the heat exchanger 36 has a plurality of radial and circular heat exchanger bellows, baffles, or convolutions 110. The heat exchange convolutions 110 are a series of circular ribs that can be seen in greater detail in FIG. 3. These circular ribs constituting the heat exchange bellows, convolutions or baffles 110 are formed as a plurality of plates or ribs 112 which circumscribe a water baffle 114. The bellows 110 are sealed by O'rings 111 and 113 at either end. The water baffle 114 serves to direct the flow of water counter-current to the flow of the blood flowing around the ribs 112. Heat exchange takes place from the interiorly heated or cooled water to the blood flowing exteriorly around the ribs 112.

The inlet of the heated water can be seen directed from the inlet 50 into the inlet of the water baffle 116 which flows into the interior portion and ribs 112 of the heat exchanger 36 and then out through the outlet connection 52 through the outlet portion extending from the water baffle 118.

An inlet 119 to the ribs 112 is formed along the length of the venous blood inlet 34. This inlet is elongated and elliptical in nature and serves to spread the blood along the extent of the ribs 112. Thus greater contact of the blood to the full extent of the ribs 112 is achieved to increase greater heat exchange between the heated or cooled water on the inside of the ribs and the blood. The blood in effect does not circumscribe the exterior of the ribs 112 in a limited extent of circular travel but spreads across their spaced distance in the longitudinal direction of inlet 34.

The outer wall 56 of the blood inlet manifold can be seen in FIGS. 2 and 3 with an elongated outlet or elliptical opening 122 through which the blood is delivered. This elongated heat exchanger outlet opening 122 can be seen as an ellipse or elongated portion or opening 124 seated below a core 126. The core 126 is internal to the housing 10 and receives a fiber bundle around it having the oxygen tubules for the oxygen transfer of this invention. The core 126 has an outer wall portion 128 that is elliptical in shape and in turn has a rib 130 to provide internal strength thereto.

The wall 128 extends downwardly to an elliptical or lower blood manifold inlet portion 124 which is formed in a lower wall portion 136 having surrounding outlets, openings, vents or windows 140. The orientation of the outlets or windows 140 around the elliptical core 126 permits flow in an initial radial manner. This allows for the flow of blood as seen by the arrows from the lower manifold chamber 124 in a well spread radial manner through a large elliptical area for introduction of the blood into the bundle of fibers at the base or introductory portion.

A base member, plate or cover 123 is shown having a cup like interior surface 125 which can be seen in FIG. 6. This cup like interior surface 125 serves to collect any plasma that migrates from the tubules or fibers 152 downwardly in the direction of oxygen flow. The plasma can be held against flow by means of a weir or dam in the form of two walls 127 and 129. These two walls 127 and 129 permit the damming of the plasma for collection through opening 69 that can be connected to a tube for the receipt thereof.

The mat of fibers is wrapped on the core 126 in a tight manner to permit the flow of blood without unnecessary channeling. This can be seen in FIG. 5 wherein tubules 152 are shown in crossed relationship to each other, and have been wrapped around the core 126 to permit the flow of gas downwardly in the direction of arrow GF (gas flow). Blood flows around the tubules 152 such as in spaces 158 between the tubules and the direction of arrow BF (blood flow).

The core 126 is seated on the base member 123 having an elliptical flange 164 with an O'ring or other seal mechanism 166 for receipt of the wall of the core there against. The base portion 123 incorporates an upward flange 164 that can be seen in greater detail in FIG. 6 as well as the inner elliptical opening 122.

The tubules or fibers 152 with the spaces 158 are wrapped tightly on the core 126 and form a plurality of layers or bundles 174. The tubules are bound in some measure by interwoven threads to hold them in the criss-cross relationship shown in FIG. 5. This criss-cross relationship is achieved by biasing the tubules 152 during the formation thereof and by stretching them against the threads holding them together in the biased angular relationship to provide the spaces 158 so that flow over the surfaces of the tubules 152 is maximized in the bundle comprising layers 174.

The formation of the bundle comprising layers 174 is sealed at the lower end by a potting compound 178 surrounding the tubules or fibers 152, and at the upper end by potting compound 180 surrounding the tubules 152. The potting compound 178 and 180 can be of a two part urethane potting solution or any other type of potting solution which allows for a sealing of the tubules 152. The respective potting of the ends of the bundle 175 allows for flow of the gas therethrough and the flow of blood once the potting material has been cut away from the axial openings of the tubules or fibers 152 comprising the layers 174.

The core 126 at its upper end comprises a flanged portion 182. The flanged portion 182 receives the cap 26 having a lower elliptical flanged or internally bossed portion 184. The elliptical flanged or bossed portion 184 aligns the lid 26 to the core 126. This also serves to provide an inlet area for the flow of oxygen in the form of a gas or oxygen manifold 186.

The side walls of the lid or cap 26 are sealed by way of depending flanges into a groove 188 of the housing 10 and sealed therein with an adhesive of a suitable nature.

Looking more particularly at the construction of the housing 10, it can be seen that the wall 22 bifurcates at ledge 100 to form a double walled construction providing for a trough, groove, or channel 192 provided by the outer wall 12 and an inner wall or dam 194. The inner wall 194 is formed to receive the bundle 175 therein and extends as an extension and is part of the wall 22.

Wall 22 with inner wall 194 are such wherein they have a draft or decrease as to their interior dimension or spacing in a slight conical relationship as they extend from the base 123 to the cap 26. This is provided by having a draft sloping inwardly toward the upper portion of the inner wall 192 from the base of the wall 22. In effect, a space 202 between the walls 22 and 194 that receives the bundle 175 slopes inwardly as it extends upwardly to the upper and inner wall 194. This interior taper of the wall 22 that extends upwardly toward the upper and inner wall 192 allows for a draft angle that can extend from ¼° to 4° toward the axis of the oxygenator. This serves to wedge the bundle 175 more compactly toward the top than at the bottom.

The introduction of the blood through the openings, vents or windows 140 in the direction of the blood arrows spreads the blood radially at the less compact area or the wider draft portion in the space 202. The spread of the blood radially through the bundle 175 extends upwardly in the direction of the arrow through the spaces 158 between the tubules 152. The net result is to provide for radial flow initially at the base of the bundle 175 so that it spreads outwardly and then upwardly in the direction of the blood flow arrows passing through the bundle 175.

Another feature of providing the inward taper or draft of the wall 22 upwardly to the inner wall 194 is to allow for easier insertion of the bundle 175 during the manufacturing process. The bundle 175 can be inserted and allow for the ingress and tight compaction toward the upper portion where the blood flows outwardly from the bundle.

Looking specifically at the oxygen inlet manifold 186 connected to the oxygen inlet 66, it can be seen that oxygen flows downwardly from the inlet manifold at the potted end 180 of the bundle 175. As the oxygen flows downwardly in the direction of the gas flow arrow GF it transfers gas from the tubules or fibers 152 to the blood flowing in the spaces 158 so that oxygenation of the blood takes place.

As the blood arrives toward the upper portion of the oxygenator, it can be seen that it flows outwardly through the spaces 158 of the tubules or fibers 152 into a space collector or blood outlet manifold 260. Blood outlet manifold or collector 260 is within the wall portion 12 that also comprises the groove or trough 192 between walls 12 and 194. The collector 260 in effect is a gas removal manifold which allows for the reduction of the blood flow velocity to allow for the emission of gaseous microemboli from the blood. The gaseous microemboli emission or disentrainment of the gas bubbles from the blood is enhanced by a sloping upper wall portion of the potted area 180 which comprises the upper wall or surface 181 of the manifold 260. The inner surface of the potted area 180 forming the upper walled portion 181 of the blood outlet manifold 260 is in alignment with line 270 seen in FIG. 3A to provide for an upward slope of anywhere from ¼° to 4° as exemplified by the lines 270 and 271. Line 272 is in alignment with the upwardly sloping edge 281 of wall 194 which slopes upwardly at anywhere from ¼° to 4°. Lines 270 and 272 extend upwardly from a plane described by lines 271 and 273 that are normal or at 90° to the axis of the oxygenator. This upward slope of the interior potted area 180 and the top 281 of wall 194 allows for the natural disentrainment of gas bubbles in the blood so that the gas will flow out of port 90 more effectively.

The upward slope of ¼° or more in the directions of lines 270 and 272 places the interior of the blood outlet manifold 260 in a manner that the gas seeks to rise to the top and flow out from the oxygenator. At the same time it can be seen that a lower channel wall 280 in channel 192 slopes downwardly in the direction of a conical outlet 284 formed by wall 74. This is further exemplified in FIGS. 4A and 4B. This conical tapering, or funneling outlet or channel 284 extends downwardly in its conical manner so that it slopes inwardly toward the outlet 76 as it extends downwardly to allow for the greater disentrainment of gas bubbles upwardly through the outlet port 90.

Figure 4:
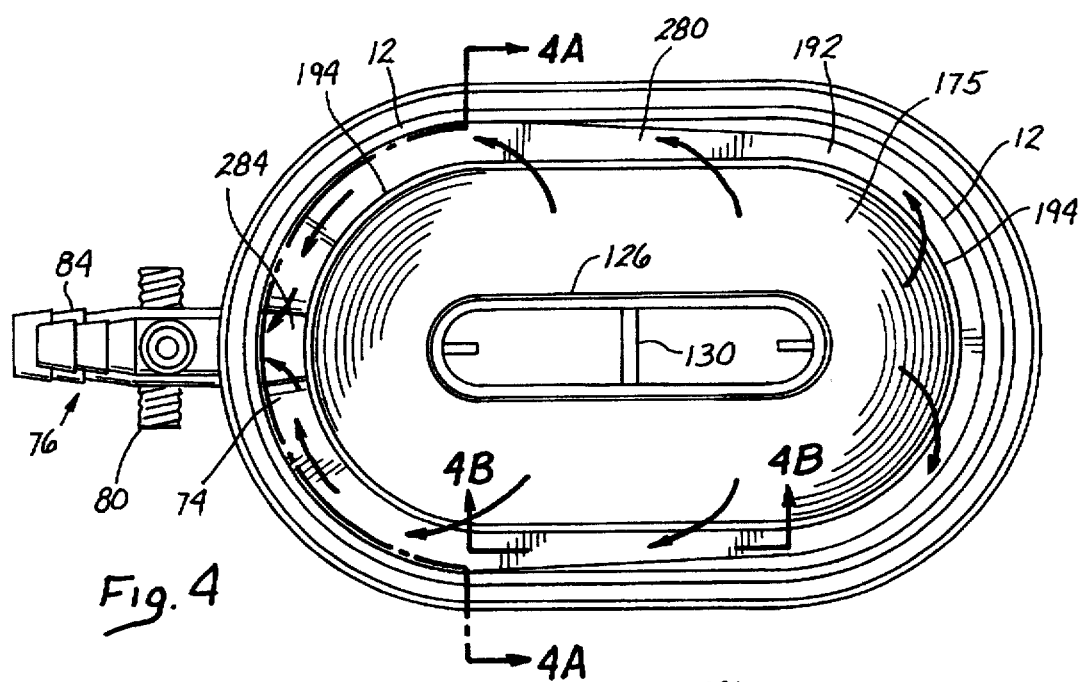
FIG. 4 shows a plan view as sectioned and looking downwardly over the flow path of blood after it emerges from the tubules of the bundle along lines 4—4 of FIG. 3.
Figure 4A:
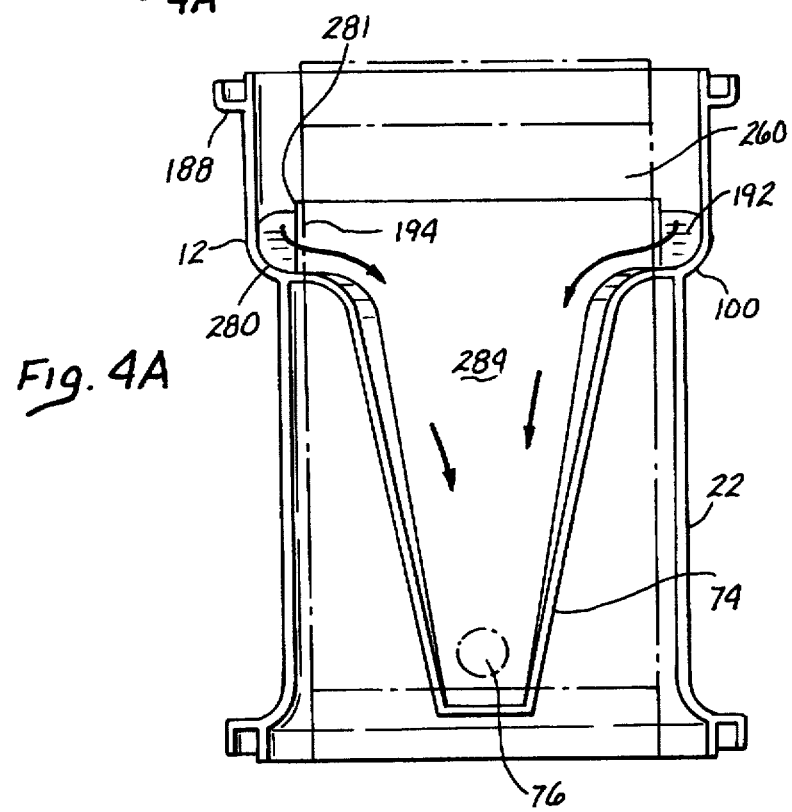
FIG. 4A shows a view looking at a sectional end elevation view along lines 4A—4A of FIG. 4.
Figure 4B:
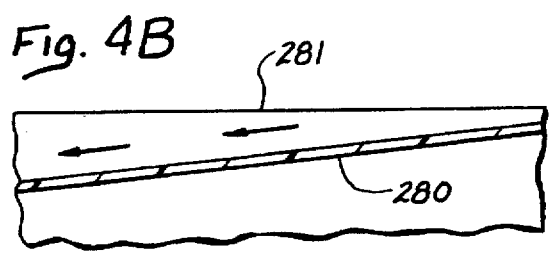
FIG. 4B shows a sectional view to illustrate the enlarged sloping path toward the outlet along lines 4B—4B of FIG. 4.

Another feature of the channel 192 is that at the portion distal or remote from the conical outlet 284, it can be seen that the depth and width between the walls of the channel namely outer wall 12 and inner wall 194 is considerably smaller than the point where they approach the downwardly conical outlet 284. The increasing width is seen in FIG. 4, while the increasing depth is seen in FIG. 3, 3A, 4A and 4B. In effect, the channel 192 extends from the portion remote from the outlet 284 in an ever expanding and deeper manner until it reaches the conical outlet. At the same time the upper surface 281 or dam of the channel 192 slopes upwardly in the direction of arrow 272 from a line 273 normal to the axis of the oxygenator. The upper surface of wall 194 extends upwardly toward outlet 284 at anywhere from ¼° to 40°. The space of the blood outlet manifold 260 between the top of wall 194 and the lower or interior wall portion 181 of the potting 180 can be relatively uniform and slope upwardly at anywhere from ¼° to 4°. This serves to provide an upwardly sloping blood outlet manifold 260.

When looking at the flow of blood, it can be seen that it flows initially through the venous connection or conduit 34 outwardly and upwardly around the ribs 112 and between them so as to become heated or cooled by the water flowing into inlet opening 50 and out of outlet 52. The blood then flows through the upper elliptical opening 122 into an opening 124. This elliptically shaped opening 122 forms part of the heat exchanger 36 and outlet 122. It serves to optimize heat exchanger efficiency to allow the blood to initially flow toward the ends of the heat exchanger rather than directly flowing merely to the middle portion. This can be seen as to the fact that the elliptical blood inlet opening 119 spreads all along the base of the ribs 112 of the heat exchanger 36.

At this flow point, the blood is spread into the elliptical introductory blood manifold formed by opening 124. As previously stated, this elliptical opening 124 provides for flow through openings or windows 140 initially radially outwardly into the bottom fibers 152 in part due to the draft of the ¼° or greater inwardly tapered slope of the wall 22 and inner wall 194.

The overall outlet area extending from the space of opening 124 is such where it should be approximately anywhere from ten percent to fifteen percent of the area of the exposed fibers opening into the upper gas removal and blood outlet manifold 260. The surface of the bundle extending above the dam or inner wall 194 to the underside 181 of the potting material 180 should be anywhere from ninety percent to one hundred percent as large as the surface area of the fiber bundle exposed at the interior of the blood introductory manifold 140. The face of the open fibers in the space of the blood outlet manifold 260 along the length of the dam provided by the upper surface 281 of inner wall 192 is greater than the heat exchanger outlet 122 and blood introductory manifold 124. This reduces the pressure drop of the oxygenator. This also serves to optimize the utilization of the fiber bundle 175.

The sloped manifold space of blood outlet manifold 260 provided in the upper portion creates a divergent angle toward the blood air outlet vent 90 and the conical outlet flow path 284 to the arterial blood outlet 76. This upwardly divergent angle in the direction of lines 270 and 272 that is sloped upwardly to provide the blood outlet manifold space 260 and upwardly sloping direction toward the outlet 90 aids in priming as well as the gaseous microemboli disentrainment and removal. The net result is a divergent blood flow path downwardly and along the bottom 280 of the channel 192, with gas bubbles passing preferentially upwardly towards and outwardly through the outlet 90.

Another feature of the invention is the orientation of the ports for the blood being on one side, namely ports 34, 76 and 90. The oxygen or gas ports in the form of ports 66 and 68 are on the opposite side overlaying the inlet and outlet water vents 50 and 52. The funnel shape of the channel 284 within the double walls 74 and 192 provides for the divergent flow of blood with the attendant divergent disentrainment of gaseous microemboli. This also helps to remove blood stagnation and reduces pressure drop.

From the foregoing, it can be seen that the orientation of the oxygenator with the improved inlet of blood into the bundle 175 to provide for radial flow and then axial flow arriving at a manifold at the top significantly greater than the blood inlet manifold allows for disentrainment of gaseous microemboli while at the same time providing for high efficiency ratios. It is believed that the foregoing angular configurations and orientation are significant steps over the art and should be read broadly in light of the following claims.

We claim:

1. An oxygenator for oxygenating blood comprising:
   a housing having an outer walled portion and a top portion and bottom portion, and a trough and funnel portion in fluid communication with an outlet;
   means for introducing blood through the bottom portion of said housing;
   means for oxygenating the blood within said housing as it moves upwardly through said housing;
   blood outlet manifold in the upper portion of said housing in fluid communication to said outlet on one end;
   said blood outlet manifold having upper and lower walls which increase in distance between said walls towards said outlets; and wherein,
   said trough forms at least in art said lower wall and is larger in volume toward said outlet.

2. The oxygenator as claimed in claim 1 wherein:
   said blood outlet manifold in part comprises said trough which increases toward the funnel portion in depth from a point removed from the blood outlet of said manifold.

3. The oxygenator as claimed in claim 1 further comprising:
   a blood outlet manifold having a reservoir formed in part as said trough which increases in width and depth toward said funnel portion from a point removed from the outlet.

4. The oxygenator as claimed in claim 3 wherein:
   said funnel portion narrows downwardly toward said outlet.

5. The oxygenator as claimed in claim 1 wherein:
   said funnel portion narrows toward said outlet.

6. The oxygenator as claim in claim 1 further comprising:
   said blood outlet manifold having an upper wall angled upwardly in the direction toward said funnel portion.

7. The oxygenator as claimed in claim 1 further comprising:
   a fiber bundle within said oxygenator between the inlet and the blood outlet manifold having a plurality of fibers for the transfer of oxygen to blood;
   means for providing oxygen to said fibers; and,
   an inlet means to said fibers of anywhere from ten percent to fifteen percent of the surface area of the fibers in adjacent flowing relationship to said blood outlet manifold.

8. The oxygenator as claimed in claim 7 further comprising:
   a wall surrounding said fibers having a narrowing smaller dimension as said walls extend toward said blood outlet manifold.

9. An oxygenator for oxygenating blood comprising:
   a housing having walls forming a portion of said housing terminating at a top portion and a bottom portion;
   a fiber bundle extending between said walls;
   means to deliver blood to said fiber bundle for flowing blood upwardly though said fiber bundle;
   means to deliver oxygen for flowing oxygen downwardly through said fiber bundle for oxygenating blood flowing through said fiber bundle;
   a blood outlet manifold adjacent the top portion of said fiber bundle formed with an interior upper wall that slopes upwardly for the disentrainment of gaseous microemboli;
   a downwardly extending narrowing funnel portion connected to said blood outlet manifold; and,
   means for removing gaseous microemboli from said blood outlet manifold.

10. The oxygenator as claimed in claim 9 further comprising;
    a downwardly extending narrowing funnel shaped passage connected to said blood outlet manifold for receiving blood therefrom.

11. The oxygenator as claimed in claim 10 further comprising:
    a blood outlet manifold having a reservoir extending from one side thereof to said funnel portion with increased volume.

12. The oxygenator as claimed in claim 12 wherein;
    said reservoir has increased width in the form of a channel extending toward said funnel portion.

13. The oxygenator as claimed in claim 11 wherein:
    said reservoir has increased depth toward said funnel portion.

14. The oxygenator as claimed in claim 11 further comprising;

a blood outlet manifold formed with an interior and exterior wall which forms said trough for receiving blood therein to provide said reservoir.

15. The blood oxygenator as claimed in claim 14 further comprising:

a heat exchanger in connected relationship to said blood oxygenator; and, means for delivering blood from said heat exchanger to said blood oxygenator.

16. The oxygenator as claimed in claims 15 further comprising:

a heat exchanger having a plurality of ribs;

means for delivering blood substantially along said ribs for flowing blood over the surfaces thereof and allowing blood to flow from a substantial number of said ribs;

means for delivering blood to said fiber bundle through a plurality of windows; and, wherein said surface area of the fiber bundle adjacent and connected to the blood outlet manifold is in a ratio of ninety percent to one hundred percent of the surface area of the fiber bundle to which said blood is delivered.

17. A blood oxygenator for oxygenating blood comprising:

a housing having an outer wall and a top and a bottom portion;

a core with the outer wall of said housing;

a fiber bundle between said core and said outer wall; and, wherein said outer wall is sloped inwardly extending toward the top portion of said oxygenator.

18. The oxygenator as claimed in claim 17 wherein;

the slope of said outer wall is at a draft angle of ¼° to 4° toward the axis of said oxygenator.

19. The oxygenator as claimed in claim 17 further comprising:

means to deliver blood to said fiber bundle;

a blood outlet manifold adjacent said fiber bundle at the upper portion thereof surrounding said fiber bundle; and, wherein said surface area of said means to deliver blood to said fiber bundle is in a ratio of ten percent to fifteen percent of the surface area of said fiber bundle adjacent said blood outlet manifold.

20. The oxygenator as claimed in claim 19 further comprising:

a blood outlet manifold having an interior upper surface sloping upwardly toward a gas outlet.

21. The oxygenator as claimed in claim 20 further comprising:

a funnel shaped portion which decends from said blood outlet manifold in decreasing volume toward the blood outlet.

22. The oxygenator as claimed in claim 19 further comprising:

a blood outlet manifold having a reservoir formed from the outer wall of said housing and an inner wall forming a trough therebetween.

23. The oxygenator as claimed in claim 22 wherein:

said trough between said inner and outer wall increases in volume toward said funnel portion.

24. A blood oxygenator comprising:

a housing having walls and a top portion and bottom portion;

means for delivering blood to the bottom portion of said oxygenator;

a fiber bundle within said oxygenator in connected relationship to said means for delivering blood to said oxygenator;

a blood outlet manifold adjacent the upper portion of said fiber bundle; and, means for delivering blood to said fiber bundle in connected relationship to said means for delivering blood to said oxygenator having an area exposed to said fiber bundle that is ten percent to fifteen percent of the area of said blood outlet manifold adjacent the upper portion of said fiber bundle.

25. The oxygenator as claimed in claim 24 further comprising:

a blood outlet manifold formed of the outer wall of said housing and an inner wall defining a channel which increases in volume from one portion of said blood oxygenator to the other portion.

26. The oxygenator as claimed in claim 25 further comprising:

a core within said oxygenator upon which said fiber bundle is wrapped, wherein said core includes said means for delivering blood to said fiber bundle.

27. The oxygenator as claimed in claim 24 further comprising:

an angular inwardly sloping configuration to said walls extending upwardly to said blood outlet manifold wherein said fiber bundle is placed within said walls at the lower portion in a less compact manner than at the upper portion.

* * * * *

UNITED STATES PATENT AND TRADEMARK OFFICE
CERTIFICATE OF CORRECTION

PATENT NO. : 5,762,869

DATED : June 9, 1998

INVENTOR(S) : George W. White, Brian M. Raze, Jeffrey P. DuMontelle

Page 1 of 2

It is certified that error appears in the above-indentified patent and that said Letters Patent is hereby corrected as shown below: In the Drawing:

the drawing should appear as follows:

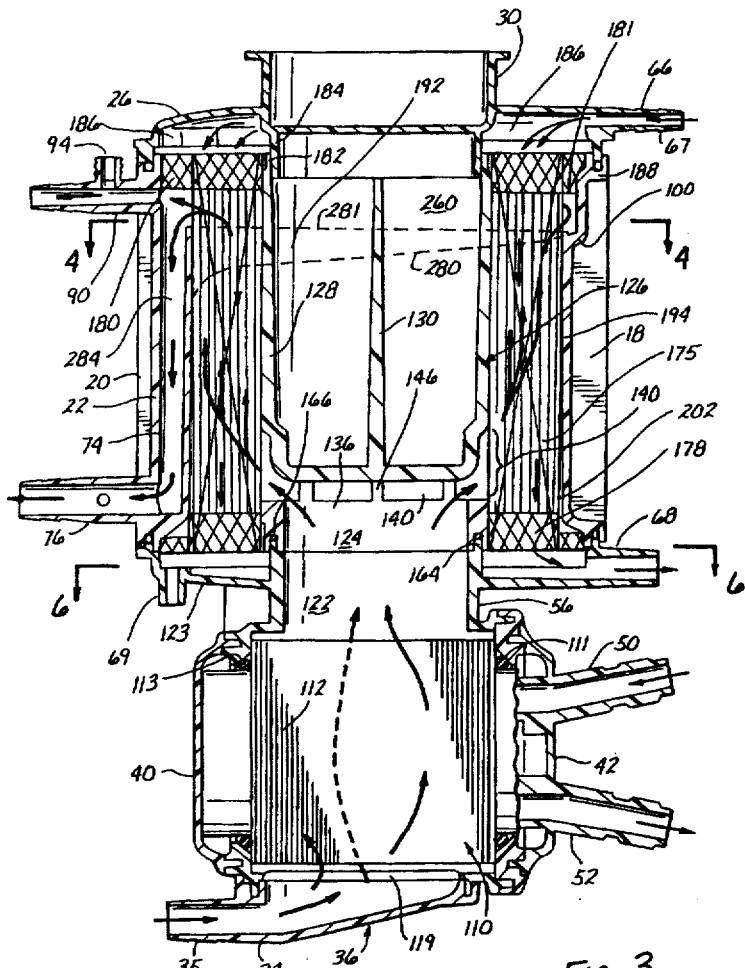

Fig. 3

UNITED STATES PATENT AND TRADEMARK OFFICE
CERTIFICATE OF CORRECTION

PATENT NO. : 5,762,869
DATED : June 9, 1998
INVENTOR(S) : George W. White, Brian M. Raze, Jeffrey P. DuMontelle It is certified that error appears in the above-indentified patent and that said Letters Patent is hereby corrected as shown below:

Column 3, line 5, after "microemboli" insert the following: --entrained blood. This is done through its connections to an--.

Column 8, line 39, after "to" delete "40°" and insert --4°--.

Column 9, line 55, insert --a-- at the beginning of the line before "blood"; line 59, correct "outlets" to read --outlet--; line 60, after "in" correct "art" to read --part--.

Column 10, line 7, delete "3" and insert --1--; line 8, delete "downwardly"; line 10, delete "1" and insert --3--; line 11, after "narrows" insert --downwardly--; line 55, delete "10" and insert --9--; line 59, delete "12" and insert --11--.

Signed and Sealed this

Seventeenth Day of August, 1999

Attest:

Q. TODD DICKINSON

*Attesting Officer*  *Acting Commissioner of Patents and Trademarks*